US00PP18612P2

(12) United States Plant Patent
Klemm

(10) Patent No.: US PP18,612 P2
(45) Date of Patent: Mar. 18, 2008

(54) *NEMESIA* PLANT NAMED 'KLENH05138'

(50) Latin Name: *Nemesia hybrida*
Varietal Denomination: KLENH05138

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 11/583,641

(22) Filed: Oct. 19, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Nemesia* plant named 'KLENH05138', characterized by its upright, outwardly spreading and compact growth habit; freely branching and flowering plant habit; and violet blue-colored flowers.

1 Drawing Sheet

Botanical designation: *Nemesia hybrida.*
Cultivar denomination: 'KLENH05138'.

BACKGROUND OF THE INVENTION

The present invention relates to a new and distinct cultivar of *Nemesia,* botanically known as *Nemesia hybrida* and hereinafter referred to by the name 'KLENH05138'.

The new *Nemesia* is a product of a planned breeding program conducted by the Inventor in Stuttgart, Germany. The objective of the breeding program is to create new compact *Nemesia* cultivars with good vigor and attractive flower coloration.

The new *Nemesia* originated from an open-pollination in June, 2002 in Stuttgart, Germany of a proprietary selection of *Nemesia hybrida* identified as code number V 032, not patented, as the female, or seed, parent with an unknown selection of *Nemesia hybrida* as the male, or pollen, parent. The new *Nemesia* was discovered and selected by the Inventor as a single flowering plant within the progeny of the stated open-pollination in a controlled environment in Stuttgart, Germany in June, 2003.

Asexual reproduction of the new *Nemesia* by terminal cuttings in a controlled environment in Stuttgart, Germany since September, 2003, has shown that the unique features of this new *Nemesia* are stable and reproduced true to type in successive generations.

SUMMARY OF THE INVENTION

The cultivar KLENH05138 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'KLENH05138'. These characteristics in combination distinguish 'KLENH05138' as a new and distinct cultivar of *Nemesia:*

1. Upright, outwardly spreading and compact growth habit.
2. Freely branching and flowering plant habit.
3. Violet blue-colored flowers.

Plants of the new *Nemesia* differ from plants of the female parent selection in the following characteristics:

1. Plants of the new *Nemesia* are larger than plants of the female parent selection.
2. Plants of the new *Nemesia* have larger flowers than plants of the female parent selection.

Plants of the new *Nemesia* can be compared to plants of the cultivar KLENE04146, disclosed in U.S. Plant patent application Ser. No. 11/343,865. In side-by-side comparisons conducted by the Inventor in Stuttgart, Germany, plants of the new *Nemesia* differed from plants of the cultivar KLENE04146 in the following characteristics:

1. Plants of the new *Nemesia* were larger than plants of the cultivar KLENE04146.
2. Plants of the new *Nemesia* and the cultivar KLENE04146 differed in flower color.

BRIEF DESCRIPTION OF THE PHOTOGRAPH

The accompanying colored photograph illustrates the overall appearance of the new *Nemesia,* showing the colors as true as it is reasonably possible to obtain in colored reproductions of this type. Colors in the photograph may differ slightly from the color values cited in the detailed botanical description which accurately describe the colors of the new *Nemesia.* The photograph comprises a close-up view of a typical flowering plant of 'KLENH05138' grown in a container.

DETAILED BOTANICAL DESCRIPTION

The photograph and following observations, measurements and values describe plants grown in Stuttgart, Germany in containers in a glass-covered greenhouse during the spring and under conditions which closely approximate commercial production. During the production of the plants, day temperatures ranged from 18° C. to 22° C., night temperatures ranged from 12° C. to 18° C. and maximum light levels were 60,000 lux. Plants were pinched one time and were about eleven weeks old when the photograph and the description were taken. In the description, color references are made to The Royal Horticultural Society Colour Chart, 1995 Edition, except where general terms of ordinary dictionary significance are used.

Botanical classification: *Nemesia caerulea* cultivar KLENH05138.

Parentage:

*Female, or seed, parent.*—Proprietary selection of *Nemesia hybrida* identified as code number V 032, not patented.

*Male, or pollen, parent.*—Unknown selection of *Nemesia hybrida,* not patented.

Propagation:

*Type.*—By terminal cuttings.

*Time to initiate roots, summer.*—About six days at 25° C.

*Time to initiate roots, winter.*—About ten days at 25° C.

*Time to produce a rooted young plant, summer.*—About ten days at 25° C.

*Time to produce a rooted young plant, winter.*—About 14 days at 25° C.

*Root description.*—Fine, fibrous; pale white in color.

*Rooting habit.*—Freely branching; dense.

Plant description:

*Plant and growth habit.*—Upright, outwardly spreading and compact growth habit. Freely branching; about 10 to 15 primary branches develop per pant. Vigorous growth habit.

*Plant height.*—About 15 cm to 17 cm.

*Plant diameter.*—About 20 cm to 22 cm.

Lateral branch description:

*Length.*—About 13 cm.

*Diameter.*—About 2 mm.

*Internode length.*—About 7 mm.

*Strength: Moderately strong.*

*Aspect.*—Initially upright to outwardly spreading.

*Texture.*—Smooth, glabrous.

*Color.*—146B.

Foliage description:

*Arrangement.*—Opposite, simple; sessile.

*Length.*—About 1.6 cm.

*Width.*—About 8 mm.

*Shape.*—Lanceolate.

*Apex.*—Cuspidate.

*Base.*—Truncate.

*Margin.*—Serrate.

*Texture, upper and lower surfaces.*—Smooth, glabrous.

*Venation pattern.*—Pinnate; arcuate.

*Color: Developing foliage, upper surface:* 137C. Developing foliage, lower surface: 139C. Fully expanded foliage, upper surface: 137A; venation, 137C. Fully expanded foliage, lower surface: 137C; venation, 137C.

Flower description:

*Flower arrangement and habit.*—Zygomorphic solitary flowers arranged on terminal racemes; flowering acropetally towards the apex. Flowers bilabiate. Flowers face mostly outwardly. Flowers last about one week on the plant. Flowers not persistent. Freely flowering habit with about 36 open flowers and flower buds per raceme.

*Fragrance.*—Faint; floral.

*Natural flowering season.*—In Germany, plants flower from May through September; flowering continuous during this period.

*Inflorescence height.*—About 4 cm.

*Inflorescence diameter.*—About 2 cm.

*Flower diameter.*—About 1.3 cm.

*Flower depth.*—About 1.4 cm.

*Flower throat diameter.*—About 3 mm.

*Flower tube length.*—About 5 mm.

*Flower tube diameter, base.*—About 1 mm.

*Flower buds.*—Shape: Ovate. Length: About 4 mm. Diameter: About 3 mm. Color: 138D.

*Petals.*—Arrangement: Five petals; four upper petals are fused at base to form an upright lobed and arched banner lip; lower petal modified into a larger lip with convex oval protuberance with serves as a pollinator nectar guide and landing platform. Shape: Ovate. Apex: Obtuse. Margin: Entire. Length: Upper petals: About 8 mm. Lower petal: About 1 cm. Width: Upper petals: About 5 mm. Lower petal: About 1.5 cm. Texture, upper and lower surfaces: Smooth, glabrous; velvety. Color: When opening, upper surface: 86B. When opening, lower surface: 86C. Fully opened, upper surface: 90B, protuberance, close to 8D; throat, 97A. Fully opened, lower surface: 90D; tube, 138D.

*Sepals.*—Arrangement: Calyx star-shaped with five sepals fused at the base. Shape: Lanceolate. Apex: Cuspidate. Margin: Entire. Length: About 2 mm. Width: About 1 mm. Texture, upper and lower surfaces: Smooth, glabrous; velvety. Color, upper surface: 138A. Color, lower surface: 139B.

*Peduncles.*—Length: About 2 cm. Diameter: About 1 mm. Angle: Erect. Strength: Strong. Texture: Smooth, glabrous. Color: 138A.

*Pedicels.*—Length: About 8 mm. Diameter: About 0.5 mm. Angle: Erect. Strength: Moderately strong. Texture: Smooth, glabrous. Color: 138A.

*Reproductive organs.*—Stamens: Quantity/arrangement: Four per flower. Anther shape: Elliptic. Anther length: About 1 mm. Anther color: 157B. Pollen amount: Scarce. Pollen color: 12B. Pistils: Quantity: One per flower. Pistil length: About 2 mm. Style length: About 1 mm. Style color: 144C. Stigma shape: Ovate. Stigma color: 144C. Ovary color: 146D. Seed/fruit: Seed and fruit development have not been observed on plants of the new *Nemesia.*

Pathogen/pest resistance: Plants of the new *Nemesia* have not been observed to be resistant to pests and pathogens common to *Nemesia.*

Garden performance: Plants of the new *Nemesia* have been observed to tolerate wind and rain and have good garden performance.

Temperature tolerance: Plants of the new *Nemesia* have been observed to tolerate temperatures from about 5° C. to about 35° C.

It is claimed:

1. A new and distinct *Nemesia* plant named 'KLENH05138' as illustrated and described.

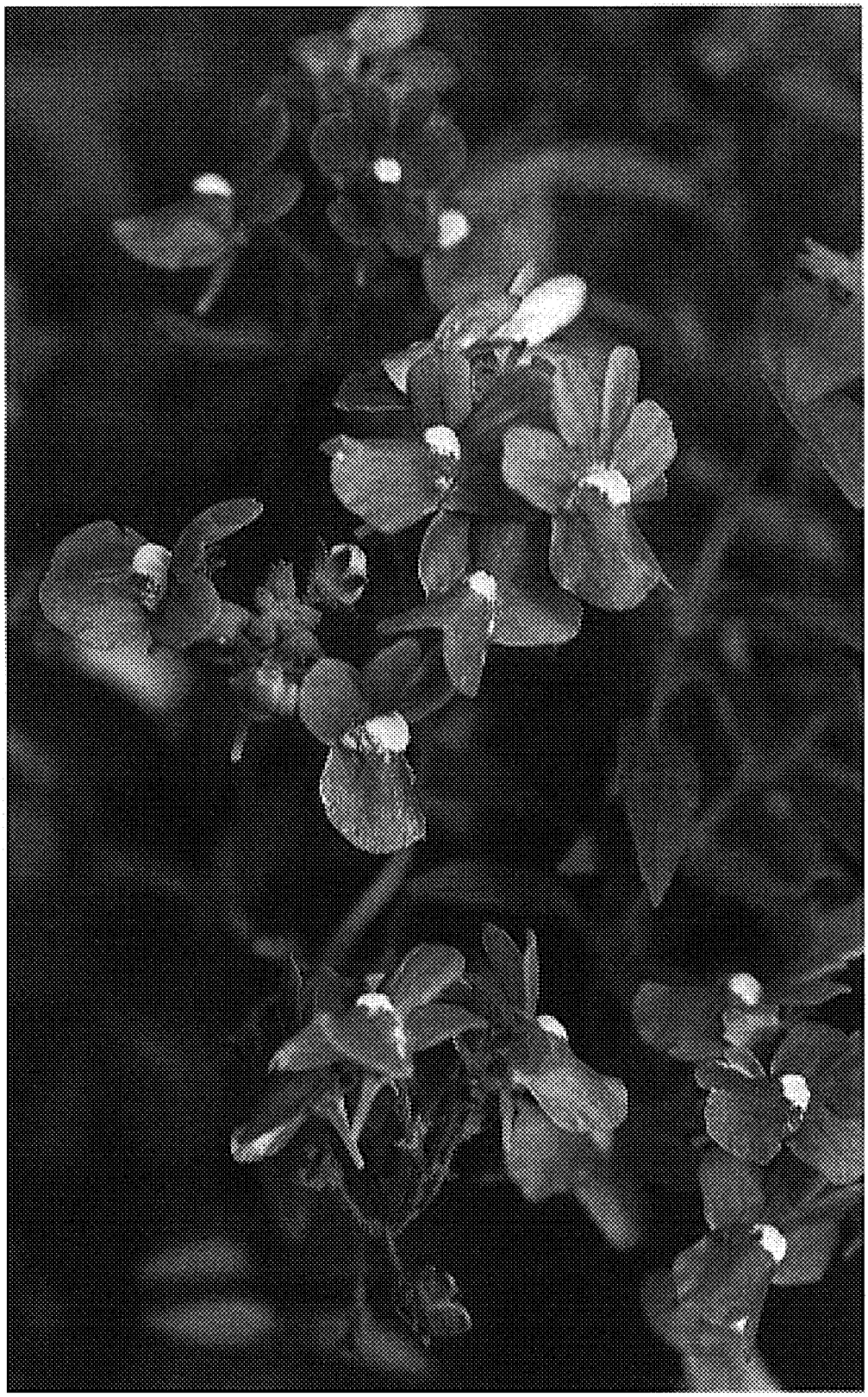

* * * * *